United States Patent [19]

Berntsson et al.

[11] 4,145,442

[45] Mar. 20, 1979

[54] PHENOXY-HYDROXYPROPYLAMINES, THEIR PREPARATION, AND METHOD AND PHARMACEUTICAL PREPARATIONS FOR TREATING CARDIOVASCULAR DISEASES

[75] Inventors: Peder B. Berntsson, Vastra Frolunda; Arne E. Brandstrom, Goteborg; Enar I. Carlsson, Kungsbacka; Stig Å. I. Carlsson, Molnlycke; Lars Ek, Onsala; Benny R. Samuelsson, Pixbo; Sven E. Sjostrand, Kungsbacka; Gert C. Strandlund, Molndal; Bengt A. H. Åblad, Goteborg, all of Sweden

[73] Assignee: Aktiebolaget Hassle, Molndal, Sweden

[21] Appl. No.: 719,345

[22] Filed: Aug. 31, 1976

Related U.S. Application Data

[63] Continuation-in-part of Ser. No. 347,625, Apr. 4, 1973, Pat. No. 3,996,382.

[30] Foreign Application Priority Data

Apr. 4, 1972 [SE] Sweden .............................. 4321/72

[51] Int. Cl.$^2$ .................... A61K 31/135; C07C 93/06
[52] U.S. Cl. ................................ 424/330; 260/307 C; 260/348.57; 260/501.17; 260/501.19; 260/562 R; 260/567.5; 260/570.7; 260/600 R; 424/316
[58] Field of Search ...................... 260/301.17, 501.19, 260/570.7; 424/316, 330

[56] References Cited

U.S. PATENT DOCUMENTS

| | | | |
|---|---|---|---|
| 3,275,654 | 9/1966 | Wilhelm et al. | 260/326.14 |
| 3,644,469 | 2/1975 | Koppe et al. | 260/570.7 X |
| 3,755,413 | 8/1973 | Koppe et al. | 260/570.7 X |
| 3,876,802 | 4/1975 | Brandstrom et al. | 260/570.7 X |

*Primary Examiner*—Robert V. Hines
*Attorney, Agent, or Firm*—Brumbaugh, Graves, Donohue & Raymond

[57] ABSTRACT

Ortho-para-substituted phenoxy-hydroxypropylamines having the general formula

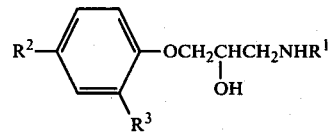

and pharmaceutically acceptable, non-toxic acid addition salts thereof, wherein $R^1$ is alkyl or hydroxyalkyl, $R^2$ is alkoxyalkyl or alkylthioalkyl, and $R^3$ is halogen, alkyl, alkenyl, alkinyl, alkoxymethyl, or alkoxy are disclosed, as are methods for their preparation.

Pharmaceutical preparations are prepared whose active ingredients include at least one of the newly discovered phenoxy-hydroxypropylamine compounds. Therapeutically effective doses of these preparations selectively block the β-receptors of the heart making them useful in treating heart diseases in animals including humans.

40 Claims, No Drawings

PHENOXY-HYDROXYPROPYLAMINES, THEIR PREPARATION, AND METHOD AND PHARMACEUTICAL PREPARATIONS FOR TREATING CARDIOVASCULAR DISEASES

The benefit of the filing date of our copending continuation-in-part application, Serial No. 347,625, filed April 4, 1973 and now U.S. Patent No. 3,996,382, is hereby claimed pursuant to 35 U.S.C. 120 and 121.

The present invention relates to new amines of formula I

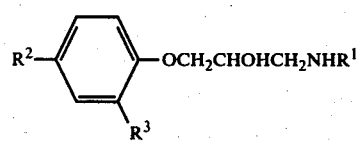
(I)

wherein $R^1$ is alkyl or hydroxyalkyl, $R^2$ is alkoxyalkyl or alkylthioalkyl, $R^3$ is halogen, alkyl, alkenyl, alkinyl, alkoxymethyl or alkoxy and a process for their preparation.

Above and below the terms alkyl, alkoxy, alkenyl and alkinyl will be understood to be such as those having up to 4 carbon atoms. Thus, when $R^1$ is alkyl, it has suitably up to 4 carbon atoms. It may be straight or branched, especially branched at the alpha carbon atom. Examples are sec-butyl or tert.-butyl or isopropyl.

When $R^1$ is hydroxyalkyl, it has up to 4 carbon atoms. It may be straight or branched, especially branched at the alpha carbon atom. Examples are 1-hydroxypropyl-2 or 1-hydroxy-2-methyl-propyl-2.

When $R^2$ is alkoxyalkyl, it has in its lower alkoxy part up to 4 carbon atoms, such as iso- or n-propyl and straight or branched butyl. Ethyl and methyl are particularly preferred.

The alkly part of the alkoxyalkyl $R^2$ group has up to 4 carbon atoms and is branched or a straight alkylene, especially ethylene-1,2,butylene-1,4 or preferably propylene-1,3. Examples of suitable alkoxyalkyl radicals are methoxymethyl, 1,2-methoxyethyl, 2-ethoxyethyl, 3-ethoxy-n-propyl, 4-methoxy-n-butyl, and especially 3-methoxy-n-propyl.

When $R^2$ is alkylthioalkyl, the hydrocarbon part of the alkylthio part and the alkyl part carrying the alkylthio part are analogous to the alkoxyalkyl $R^2$. Examples of preferred alkylthioalkyl groups are methylthiomethyl, 2-methylthioethyl, 2-ethylthioethyl, 3-ethylthio-n-propyl, 4-methylthio-n-butyl, and 3-methylthio-n-propyl.

Examples of $R^3$ when halogen are fluro, bromo and preferably chloro. When $R^3$ is alkyl, it has up to 4 carbon atoms. Examples are iso- and n-propyl and straight or branched chain butyl. Ethyl and methyl are preferred.

When $R^3$ is alkenyl, it has 2 to 4 carbon atoms. Examples are 2-methylvinyl, methallyl and preferably allyl.

When $R^3$ is alkinyl, it has 2 to 4 carbon atoms. Examples are 1-propinyl, 2-propinyl and ethinyl.

When $R^3$ is alkoxymethyl, its alkoxy part has up to 4 carbon atoms. Examples are ethyl, iso- or n-propyl, and methyl. Ethoxymethyl and methoxymethyl are preferred.

When $R^3$ is alkoxy, it has up to 4 carbon atoms. Exampls are ethoxy, iso- or n-propoxy, and preferably methoxy.

A preferred group of amines are those according to formula Ia

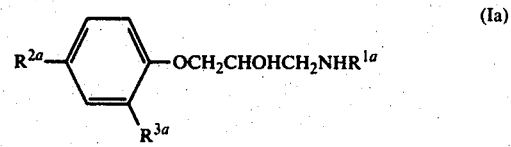
(Ia)

wherein $R^{1a}$ is alkyl having 1 to 4 carbon atome or hydroxyalkyl having 1 to 4 carbon atoms, $R^{2a}$ is alkoxyalkyl having up to 8 carbon atoms and $R^{3a}$ is halogen, alkyl having 1 to 4 carbon atoms, alkenyl having 2 to 4 carbon atoms, alkoxymethyl having up to 5 carbon atoms or alkoxy having 1 to 4 carbon atoms.

In the compounds of formula Ia, $R^{1a}$ may be a tert.-butyl, isopropyl, 1-hydroxypropyl-2 or 1-hydroxy-2-methyl-propyl-2; $R^{2a}$ may be methoxymethyl, 2-methoxyethyl, 3-methoxy-n-propyl, or 4-methoxy-n-butyl; and $R^{3a}$ may be a chloro, bromo, methyl, allyl, methoxymethyl or methoxy.

Another preferred group of amines are those according to formula Ib

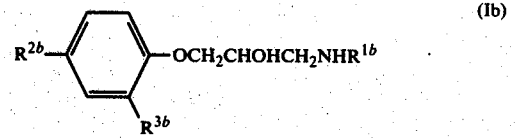
(Ib)

wherein $R^{1b}$ is alkyl having 1 to 4 carbon atoms, or hydroxyalkyl having 1 to 4 carbon atoms; $R^{2b}$ is alkylthioalkyl having up to 8 carbon atoms; and $R^{3b}$ is halogen, alkyl having 1 to 4 carbon atoms, alkenyl having 2 to 4 carbon atoms, alkoxymethyl having up to 5 carbon atoms, and alkoxy having 1 to 4 carbon atoms.

In compounds of formula Ib, $R^{1b}$ may be tert.-butyl, isopropyl, 1-hydroxy-propyl-2, or 1-hydroxy-2-methyl-propyl-2; $R^{2b}$ may be methylthiomethyl, 2-methylthioethyl, 3-methylthio-n-propyl, or 4-methylthio-n-butyl and $R^{3b}$ may be chloro, bromo, methyl, allyl, methoxymethyl, methoxy or allyloxy. Preferably, $R^{1b}$ is tert.-butyl or isopropyl; $R^{2b}$ is 2-methylthioethyl or 3-methylthio-n-propyl; and $R^{3b}$ is chloro, bromo, methyl, allyl, methoxymethyl, or methoxy.

The following compounds are especially mentioned:

(1) 1-[2-bromo-4-(2-methoxyethyl)-phenoxy]-3-isopropylamino-propanol-2

(2) 1-[2-chloro-4-(2-methoxyethyl)-phenoxy]-3-isopropylamino-propanol-2

(3) 1-[2-chloro-4-(2-methoxyethyl)-phenoxy]-3-tert.-butylamino-propanol-2

(4) 1-[2-methoxymethyl-4-(2-methoxyethyl)-phenoxy]-3-isopropylamino-propanol-2

(5) 1-[2-allyl-4-(3-methoxy-n-propyl)phenoxy]-3-isopropylamino-propanol-2

(6) 1-[2-chloro-4-(3-methoxy-n-propyl)-phenoxy]-3-isopropylamino-propanol-2

(7) 1-[2-bromo-4-(3-methoxy-n-propyl)-phenoxy]-3-isopropylamino-propanol-2

(8) 1-[2-methoxy-4-(methoxymethyl)-phenoxy]-3-isopropylamino-propanol-2

(9) 1-[2-allyl-4-(2-methoxyethyl)-phenoxy]-3-isopropylamino-propanol-2

(10) 1-[2-n-propyl-4-(2-methoxyethyl)-phenoxy]-3-isopropylamino-propanol-2
(11) 1-[2-fluoro-4-(2-methylmercaptoethyl)-phenoxy]-3-isopropylamino-propanol-2
(12) 1-[2-methoxy-4-(3-methoxy-n-propyl)-phenoxy]-3-isopropylamino-propanol-2
(13) 1-[2-fluoro-4-(2-methoxyethyl)-phenoxy]-3-isopropylamino-propanol-2.

The new compounds have valuable pharmacological properties. Thus, they block cardial β-receptors, which is shown by the fact that an intravenous dose of 0.002 to 5 mg/kg will antagonize the tachycardia caused by an intravenous injection of 0.5 μg/kg of d/1-isoproterenol sulphate on an anesthetized cat. Vascular β-receptor blockade is shown by the determination that 3 mg/kg or more of the above compounds will antagonize vasiodilation caused by an intravenous injection of 0.5 μg/kg of d/1-isoproterenol sulphate on an anesthetized cat.

The compounds of this invention in a concentration of 0.03 to 1 μg/ml also have been shown in vitro to antagonize tachycardia caused by addition of 0.005 μg/ml of d/1-isoproterenol sulfate to a bath containing an isolated guinea-pig heart.

In the field of β-receptor active compounds one will find compounds of the general formula

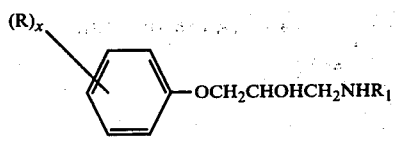

Compounds of such a formula may affect either the β-receptors in the heart (known as $β_1$ receptors) or the β-receptors in the vessels (known as $β_2$ receptors). Moreover, the β-receptor active compounds may be further sub-divided into the following categories:

A. Compounds which block the activity of the β-receptors:

A:1 Active on $β_1$-receptors
A:1:1 Active on $β_1$-receptors, no intrinsic activity
A:1:2 Active on $β_1$-receptors, intrinsic activity
A:2 Active on $β_1$-receptors and $β_2$-receptors
A:2:1 Active on $β_1$-receptors and $β_2$-receptors, no intrinsic activity
A:2:2 Active on $β_1$-receptors and $β_2$-receptors, intrinsic activity.

B. Compounds which stimulate the β-receptors (and are referred to as possessing intrinsic activity):

B:1 Active on $β_1$-receptors
B:1:1 Active on $β_1$-receptors, inotropic effect mainly
B:1:2 Active on $β_1$-receptors, chronotropic effect mainly In this respect, it may be noted that there are also compounds of somewhat differing generic formula intrinsically active on both the $β_1$ and $β_2$ receptors or intrinsically active selectively.

The compounds of the present invention are essentially pure β-receptor blocking agents which, moreover, are heart selective, i.e., at doses effective to block the β-receptors of the heart they exert relatively small effects on the $β_2$-receptors of the smooth muscles. Because the compounds of the present invention exhibit cardioselective β-blocking activities, their indicated pharmacological use is in the treatment of cardiovascular disorders, such an angina pectoris, hypertonia and heart arrythmia, while they are unsuitable for the treatment of disorders such as heart failure, normally treated with $β_1$-stimulating agents.

Based upon lboratory tests, as well as upon prior experience with other β-blocking agents, it is believed that the compounds of the present invention may be administered either intravenously or orally, with the total daily dosage in the order to 200–400 mgs. A single i.v. dosage would be in the oder to 20–40 mgs while a single oral dose would be in the order of 50–100 mgs.

The new compounds are obtained according to methods known per se. Thus, a compound of the formula II

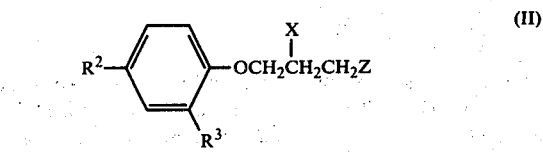

wherein $R^2$ and $R^3$ have the meanings given above, X is a hydroxy group and Z is a reactive, esterified hydroxy group or halogen, or X and Z together form an opoxy group, is reacted with an amine of the formula $NH_2$—$R^1$, wherein $R^1$ has the same meaning as given above.

A reactive, esterified hydroxy group is obtained when a hydroxy group is esterified with a strong organic sulphonic acid such as a strong aromatic sulphonic acid, e.g., benzene sulphonic acid, 4-bromobenzenesulphonic acid or 4-toluenesulphonic acid. Z being a halogen is obtained when the hydroxy group is reacted (or esterified) with a strong inorganic acid such as hydrobromic acid, hydrochloric acid or hydroiodic acid, Z being bromine, chlorine or iodine.

Z is preferably halogen, e.g., bromine, chlorine or iodine as mentioned. Thus, Z is preferably chloro, bromo or iodo.

This reaction is carried out in a common way. When using a reactive ester as a starting material the preparation takes place preferably in the presence of a basic condensing agent and/or with an excess of an amine. Suitable basic condensing agents are, e.g., alkali metal hydroxides such as sodium or potassium hydroxide, alkali metal carbonates such as potassium carbonate and alkali metal alcoholates such as sodium methylate, potassium ethylate and potassium tert.-butylate.

Further, a compound of formula III

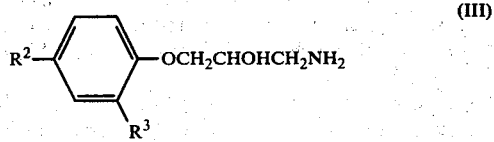

wherein $R^2$ and $R^3$ have the same meanings as given above, is reacted with a compound of the formula Z—$R^1$, wherein $R^1$ and Z have the same meanings as given above.

This reaction is carried out in a common way, preferably in the presence of a basic condensing agent and/or an excess of an amine. Suitable basic condensing agents are, e.g., alkali metal alcoholates, preferably sodium or potassium alcoholate, or also alkali metal carbonates as sodium or potassium carbonate.

Further, a compound of formula IV

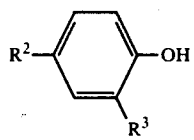

wherein $R^2$ and $R^3$ have the same meanings as given above is reacted with a compound of formula V

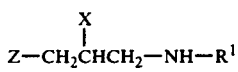

wherein Z, X and $R^1$ have the same meanings as given above.

This reaction is carried out in a common way. In those cases where reactive esters are used as starting materials, the compound of formula IV may suitably be used in the form of its metal phenolate as alkali metal phenolate, preferably sodium phenolate, or one works in the presence of an acid binding agent, preferably a condensing agent, which can form a salt of the compound of formula IV as an alkali metal alcoholate.

Further, one may split off a residue from a compound of formula I above, wherein $R^1$, $R^2$ and $R^3$ have the same meanings as above and in which the nitrogen atom of the amino group and/or the hydroxy group has attached thereto a splitable residue.

Such splitable residues are especially those which are splitable by solvolysis, reduction, pyrolysis or fermentation.

Residues splitable by solvolysis are preferably residues splitable by hydrolysis or ammonolysis.

Representative residues splitable by means of hydrolysis are: acyl residues, which, when present, are functionally varied carboxy groups; oxycarbonyl residues, such as tert.-butoxycarbonyl residue, or ethoxycarbonyl residue; aralkoxycarbonyl residues, such as phenyl-loweralkoxycarbonyl residues; a carbobenzyloxy residue; halogencarbonyl residues, such as a chlorocarbonyl residue; arylsulphonyl residues, such as toluenesulphonyl or bromobenzenesulphonyl residues; halogenated lower alkanoyl residues such as formyl-, acetyl- or trifluoroacetyl residue; and benzyl residue or cyano groups or silyl residues, such as trimethylsilyl residue.

Of the above-mentioned residues, the oxycarbonyl residues and the lower alkanoyl residues or the benzoyl residues are preferred for use.

Still other residues which may be used as alternatives to the above-mentioned residues are alkylidene or benzylidene residues or a phosphorylidene group such as a triphenylphosphorylidene group, whereby the nitrogen atom then obtains a positive charge.

Still other residues splitable at the hydroxy group or the amino group by hydrolysis are divalent residues of substituted methylenes. As substituents on the methylene residues, any organic residue may be used. Since it does not matter in the hydrolysis step which compound is on the methylene residue. As methylene substitutents, e.g., aliphatic or aromatic residues such as alkyl as mentioned above, or aryl, e.g., phenyl or pyridyl may be used. The hydrolysis may be carried out in any common way, suitably in a basic or preferably in an acid medium.

Compounds according to formula VI are also splitable by hydrolysis.

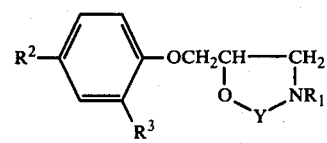

wherein $R^1$, $R^2$ and $R^3$ have the same meanings as given above and Y is a carbonyl or thiocarbonyl residue.

The hydrolysis is carrid out in an analogous way, that is, in the presence of a hydrolyzing agent. Typical hydrolyzing agents are: acidic agents, e.g., diluted mineral acids, such s sulphuric acid or hydrohalogen acid; and basic agents, e.g., alkali metal hydroxides, such as sodium hydroxide. Oxycarbonyl residues, aryl sulphonyl residues and cyano groups may be split off by means of acidic agents such s hydrohalogen acid, suitable hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). A tert.-butoxycarbonyl residue may be split off under anhydrous conditions by means of a treatment with a suitable acid, such as trifluoroacetic acid. Acidic agents are peferably used for the hydrolysis of compounds of formula VI.

Residues splitable by ammonolysis are usually the halogencarbonyl residues, such as the chlorocarbonyl residue. The ammonolysis may be carried out in a common way, e.g., by means of an amine containing at least one hydrogen atom bonded to the nitrogen atom, such as a mono- or diloweralkylamine, e.g., methylamine or dimethylamine, or especially ammonia, preferably at an elevated temperature. Instead of ammonia one may use an agent which gives ammonia, such as hexamethylenetetraamine.

Residues splitable by means of a reduction are, e.g., an α-aryl-alkyl residue, such as a benzyl residue or an α-aralkoxycarbonyl residue, such as a benzyloxycarbonyl residue, which may be split off by means of a hydrogenolysis, especially by catalytically activated hydrogen, such as by hydrogen in the presence of hydrogenating catalysts, e.g., Raney-nickel. Further residues splitable by means of hydrogenolysis are 2-halogenalkoxycarbonyl residues, such as 2,2,2-tri-chloroethoxycarbonyl residues, 2-iodoethoxy- or 2,2,2-tribromoethoxycarbonyl residues, which may be split off in a common way, suitably means of a metallic reduction (so called nascent hydrogen). Nascent hydrogen may be obtained using metal or metal alloys, such as amalgam on compounds which give hydrogen from carboxyacids, alcohols or water. Zinc or zinc-alloys together with acetic acid may be used. Hydrogenolysis of 2-halogenalkoxycarbonyl residues may further take place using chromium or chromium (II) compounds, such as chromium (II) chloride or chromium (II) acetate.

An arylsulphonyl group such as a toluenesulphonyl group may be split off by reduction, using nascent hydrogen, e.g., by means of an alkali metal, as lithium or sodium in liquid ammonia, and suitably may be split off from a nitrogen atom. In carrying out a reduction, one has to take care of the fact that other reducible groups are not influenced.

Residues splitable by means of pyrolysis, especially residues splitable from the nitrogen atom, suitably are unsubstituted or substituted carbamoyl groups. Suitable substituents are, e.g., lower alkyl or arylloweralkyl such as methyl or benzyl, or aryl such as phenyl. The pyrolysis is carried out in the usual way, whereby one may have to take care of other thermally susceptible groups.

Residues splitably by means of fermentation, especially residues splitable from the nitrogen atom, may be either unsubstituted or substituted carbamoyl groups. Suitable substituents are, e.g., lower alkyl or aryllower-alkyl, as methyl or benzyl, or aryl as pehnyl. The fermentation is carrid out in a common way, e.g., by means of the enzyme unease or soy bean extract at about 20° C. or a slighly elevated temperature.

Further, a Schiff's base of formula VII or VIII

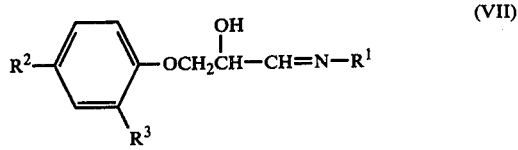

(VII)

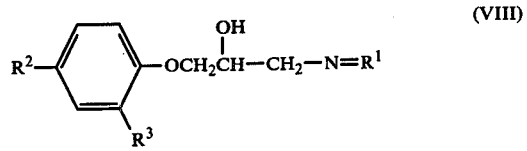

(VIII)

or a cyclic tautomer corresponding to formula VIII of formula IX

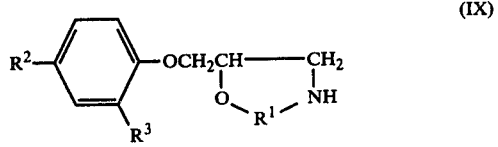

(IX)

can be reduced, wherein $R^1$, $R^2$ and $R^3$ have the same meaning as given above and $R^1$H is the same as $R^1$. The compounds of formulae VIII and IX may co-exist. This reduction is carried out in a common way, e.g., using a di-lightmetalhydride, such as sodiumboronhydride, lithiumaluminumhydride, using a hydride such as Boran with formic acid, or by means of a catalytic hydrogenation, such as with hydrogen in the presence of Raney-nickel. In such a reduction one has to take care that other groups are not affected.

In still another procedure, the oxo group in a compound of formula X

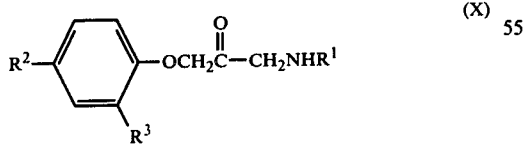

(X)

wherein $^1$, $R^2$ and $R^3$ have the same meanings as given above, can be reduced to a hydroxy group. This reduction is usually carried out especially using a di-lightmetal hydride, such as mentioned above, or according to the "Neerwein-Pondorf-Verley method", or a modification thereof, suitably using an alkanol as a reaction component and as solvent, such as isopropanol, and using a metal alkanolate, e.g., aluminum isopropanolate.

Still further, a compound of formula (XI)

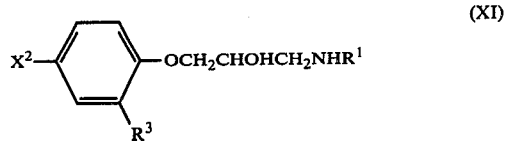

(XI)

wherein $R^1$ and $R^3$ have the same meanings as given above, and wherein $X^2$ is a residue which is able to be transformed to a residue $R^2$ having the same meaning as given above, can be used to prepare the compounds of the invention. $X^2$ is a residue transformable to $R^2$ such as $Z^1$-loweralkyl residue. Thus, a compound XI having such a $Z^1$-loweralkyl residue as $X^2$ can be racted in a common way with a compound loweralkyl-$Z^2$, whereby one of $Z^1$ and $Z^2$ is a hydroxy group or mercapto group and the other being Z having the meaning given above. Thus, one can react either a compound of formula XII

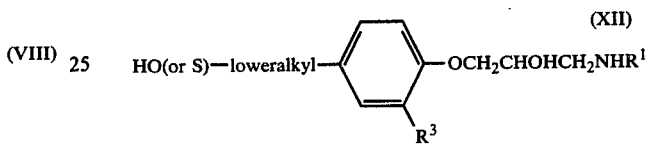

(XII)

with a compound loweralkyl-Z, or a compound of formula XIII

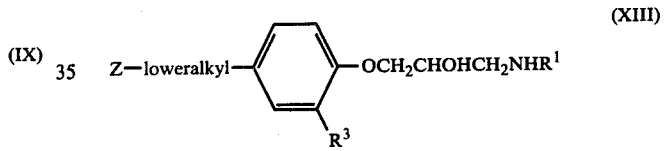

(XIII)

with a compound loweralkyl-O(S)H, whereby $R^1$, $R^3$ and Z have the meanings as given above. The reaction is carried out in a common way, e.g., as the reaction of a compound of formula II with an amine $NH_2R^1$.

Further, in still another method, the oxo group in a compound corresponding to formula I which carries an oxo group at a carbon atom bound to a nitrogen atom may be reduced to two hydrogen atoms. Such compounds are, e.g., compounds of the formula XIV

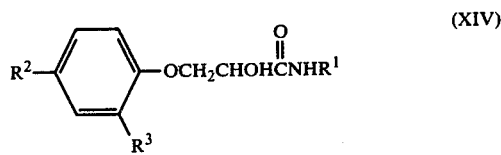

(XIV)

wherein $R^1$, $R^2$ and $R^3$ have the meaning given above. The reduction can be carried out according to the above described manner using complex metalhydrides, e.g., lithiumaluminiumhydride or di-iso-butylaluminiumhydride. Suitably the reaction takes place in an inert solvent such as an ether, e.g., diethylether or tetrahydrofuran.

A chemist will recognize that the substituents may be varied from the compounds obtained within the end product as well as the compounds obtained may be introduced, split off or transformed into other end products in a common way.

Thus, it is possible to hydrogenate catalytically C=C double bonds or C≡C triple bonds to C—C single bonds by means of hydrogen in the presence of a hydrogenation catalyst, e.g., platinum, palladium or nickel, as Raney-nickel. In such a procedure one has to take care that other reducible groups are not reduced.

A C≡C triple bond in compounds of this invention may be transformed into a C=C double bond. If desired, such hydrogenation may be effected stereospecifically into a cis- or trans-double bond. The hydrogenation of a C≡C triple bond to a C=C double bond may, for example, be carried out using 1 mole of hydrogen in the presence of a less active hydrogenation catalyst such as iron or palladium, e.g., Raney-iron or palladium with barium sulphate, preferably at an elevated temperature. The stereospecific hydrogenation to a cis double bond may take place between 1 mole of hydrogen and an only partly active catalyst, such as palladium on active carbon in the presence of quinoline, or palladium or calcium carbonate in the presence of plumbum-II salts or Raney-nickel. The hydrogenation to a trans double bond may take place by means of sodium in liquid ammonia. With regard to other reducible groups, short reaction times are usually used and no excess of the reducing agent is present. An ammonium halogenide, such as ammonium chloride, may be added as a catalyst.

In the reduction mentioned above, one has to take care that no further reducible groups are reduced. In reduction using Raney-nickel and hydrogen, one has to consider especially halogen atoms bonded to the aromatic ring, so that they are not replaced by hydrogen. Furthermore, in any reductions, especially catalytic hydrogenations, one has to consider also any thioether group present. In such cases sulphur resistant catalysts are preferably used and, after the stoichiometric amount of hydrogen is absorbed during the hydrogenation, further reduction is terminated.

The above-mentioned reactions may possibly be carried out simultaneously or in any sequence.

The above-mentioned reactions are carried out under the usual conditions well-known to chemists which may require the presence or absence of dilution, condensation and/or catalytic agents, and may require a low, room or an elevated temperature, possibly being carried out in a closed vessel, depending on specific reagents employed.

Depending on the process conditions and the starting material, the end product is obtained either in free form or in the form of its acid addition salt (which is included in the scope of the invention). Thus, for example, basic, neutral or mixed salts may be obtained as well as hemiamino, sesque- or polyhydrates. The acid addition salts of the new compounds may in a manner nown per se be transformed into free compounds using, e.g., basic agents such as alkali or ion exchanger. On the other hand, the free bases obtained may form salts with organic or inorganic acids. In the preparation of acid addition salts preferably such acids are used which form suitable therapeutically acceptable salts. Such acids are, e.g., hydrohalogen acids, sulphuric acid, phosphoric acid, nitric acid, perchloric acid, aliphatic, alicyclic, aromatic or heterocyclic carboxy or sulphonic acids, as formic, acetic, propionic, succinic, glycolic, lactic, malic, tartaric, citric, ascorbic, maleic, hydroxymaleic or pyruvic acid, phenylacetic, benzoic, p-amino-benzoic, anthranilic, p-hydroxybenzoic, salicycic or p-aminosalicyclic acid, embonic acid, methanesulphonic, ethanesulphonic, hydroxyethanesulphonic, ethylenesulphonic acids, halogenbenzenesulphonic, toluenesulphonic, naphthylsulphonic acids or sulphanilic acid; methionine, tryptohane, lysine or arginine.

These or other salts of the new compounds as, e.g., picrates may serve as purifying agents of the free bases obtained as the free bases are transformed into salts, these are separated and the bases are then set free from the salts again. According to the close relationship between the new compounds in free form and in the form of their salts, it will be understood from the above and the below that unless otherwise indicated, where specific compounds are mentioned, the corresponding salts are contemplated as well as the free compounds.

The invention also relates to any embodiment of the process in which one starts from a compound obtained as an intermediate in any process step and carries out the remaining process steps.

Thus, one may react an aldehyde of the formula XV

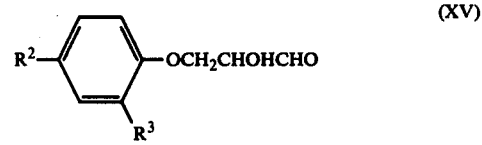

wherein $R^2$ and $R^3$ have the same meaning as given above, with an amine of the formula $H_2N-R^1$, wherein $R^1$ has the same meanings as given above, in the presence of a suitable reducing agent, as one of the above mentioned. Thereby a compound of formula VII is obtained as an intermediate, which then is reduced according to the invention.

Further, one may, in a conventional manner, react an amine of the formula III with an aldehyde or a ketone of the formula $O=R^1$, wherein $R^1$ has the above meaning in the presence of a suitable reducing agent, as one of the above mentioned. thereby, a compound of formula VIII or IX is obtained as an intermediate, which then is reduced according to the invention.

The new compounds may, depending on the choice of starting materials and process, be present as optical antipodes or racemate, or if they contain at least two asymmetric carbon atoms, be present as an isomer mixture (racemate mixture).

The isomer mixtures (racemate mixtures) obtained may, depending on physical-chemical differences of the components, be separated into the both stereoisomeric (diastereomeric) pure racemates, e.g., by means of chromatorgraphy and/or fractionated crystallization.

The racemates obtained can be separeted according to known methods, e.g., by means of recrystalization from an optically active solvent, by means of microorganisms, or by a reaction with optically active acids forming salts of the compound and separatng the salts thus obtained, e.g., by means of their different solubility in the diastereomeres, from which the antipodes by the influence of a suitable agent may be set free. Suitably useable optically active acids are, e.g., the L- and D-forms of tartaric acid, di-o-tolyl-tartaric acid, malic acid, mandelic acid, camphersulphonic acid or china acid. Preferably the more active part of the two antipodes is isolated.

Suitably such starting materials are used for carrying out the reactions of the invention, which material leads to groups of end products primarily especially desired and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as pharmaceutically acceptable, non-toxic acid addition salt, as, e.g., the hydrochloride, lactate, acetate, sulphamate or the like in combination with a pharmaceutically acceptable carrier. The carrier may be a solid, semisolid or liquid diluent. These pharmaceutical preparations are a further object of the invention. Usually the amount of active compound is between 0.1 to 95% by weight of the preparation, suitably between 0.5 to 20% by weight in preparations for injection and between 2 to 50% by weight in preparations for oral administration In the preparation of pharamaceutical preparations containing a compound of the present invention in the form of dosage units for oral administration, the compound elected may be mixed with a solid, pulverulent carrier, as, e.g. with lactose, saccharose, sorbitol, mannitol, starch, as potato starch, corn starch, amylopectic, cellulose derivatives or gelatine. An antifriction agent may also be included as magnesium stearate, calcium stearate, polyethyleneglycol waxes or the like. The preparation may then be pressed into tablets. If coated tablets are wanted, the above prepared core may be coated with concentrated solution of sugar, which solution may contain, e.g., gum arabicum, gelatine, talc, titanium dioxide or the like. Furthermore, the tablets may be coated with a laquer dissolved in a volatile organic solvent or mixture of solvents. A dye may be added to the coating in order to distinguish between tablets with different active compounds or with different amounts of the active compound present.

In the preparation of soft gelatine capsules (pearl-shaped, closed capsules), which may consist of gelatine and glycerine, the active compound is mixed with a vegetable oil. Hard gelatine capsules may contain granules of the active compund in combination with a solid, pulverulent carrier as lactose, saccharose, sorbitol, mannitol, starch (as, e.g., potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with a vegetable oil or paraffin oil.

Liquid preparations for oral administration may be present in the form of syrups or suspensions, e.g., solutions containing from about 0.2% by weight to about 20% by weight of the active substance described, whereby the residue consists of sugar and a mixture of ethanol, water, glycerol and proplyene glycol. If desired, such liquid preparations may contain coloring agents, flavoring agents, saccharine and carboxymethylcellulose as a thickening agent.

Solutions for parenteral administration by injection may be prepared as an aqueous solution of a water soluble pharmaceutically acceptable salt of the active compound, preferably in a concentration from about 0.5% by weight to about 20% by weight. These solutions may also contain stabilizing agents and/or buffering agents and may suitably be available in different dosage unit ampoules.

The preparation of pharmaceutical tablets for peroral use is carried out in accordance with the following method:

The solid substances included are ground or sieved. The binding agent is homogenized and suspended in solvent. The therapeutic compound and necessary auxiliary agents are continuously and constantly mixed with the binding agent solution, and are moistened so that the solution is uniformly divided in the mass without overmoistening any parts. The amount of solvent is such that the resulting mass has a consistency of wet snow. The moistening of the pulverulent mixtue with the binding agent solution causes the particles to gather together slightly to aggregates. The mass is then pressed through a sieve having a mesh size of about 1 mm. and placed in thin layers on a tray to be dried in a drying cabinet. This drying usually takes place about 10 hours. It should be standardized since the dampness of the granulate is of importance for the following steps. Drying in a fluid bed may be used. In this case the mass is not put on a tray but is poured into a container having a net bottom.

After the drying step, the granules are sieved. Under certain circumstances powder has to be removed.

Tp the so-called final mixture, disintegration, lubricants and antiadhesive agents are added, and the resulting mixture is formed into tablets.

The cleaned tablet punching machine is provided with a set of punches and dies, and the weight of the tablets and the degree of compression is set. The weight of the tablet depends on the size of the dose in each tablet and is calculated starting from the amount of therapeutic agent in the granules. The degree of compression affects the size of the tablet, its strength and its ability to disintegrate in water. Accordingly, the choice of compression pressure (0.5 to 5 ton) is a balance-step. When the right adjustment is set, the preparation of tablets is started.

The tablets are freed from adhering pulver and are then stored in closed packages until they are delivered.

Many tablets, especially those which are rough or bitter, are coated with a coating such as a layer of sugar.

The daily dose of the active substance varies and is dependent on the type of administration, but as a general rule it is 100 to 400 mg/day of active substance at peroral administration and 5 to 20 mg per day at intravenous administration.

The following illustrates the principle and the adaptation of the invention, however, without being limited thereto. Temperature is given in degree Centigrade.

EXAMPLE 1

1,2-epoxy-3-[2'-bromo-4'-($\beta$-methoxyethyl)-phenoxy]-propane (20.5 g) was mixed with 25 ml of isopropanol and 25 ml of isopropylamine. The mixture is then heated on a boiling waterbath for 3 hours under reflux. Thereupon the reaction mixture is evaporated to dryness and the residue is dissolved in ether and the hydrochloride precipitates on the addition of gaseous HCl in ether at pH 4–5. After recrystallization from methylethyl ketone the hydrochloride of 1-isopropylamino-3-[2'-bromo-4'-($\beta$-methoxyethyl)-phenoxy]-propanol-2 is obtained. Melting point 140° C. Equ. weight: found 383, calculated 383.

In accordance with the method of example 1, the following compounds are obtained as hydrochlorides:

EXAMPLE 2

1-isopropylamino-3-[2'-chloro-4'-(2-methoxyethyl)-phenoxy]-propanol-2. Melting point 140° C. Equ. weight: found 338, calculated 338.

EXAMPLE 3

1-tert.-butylamino-3-[2'-(2-methoxyethyl)-phenoxy]-propanol-2. Melting point 106° C. Equ. weight: found 353, calculated 352. Tert.-butylamine has been used instead of iospropylamine of Example 1.

EXAMPLE 4

1-isopropylamino-3-[2'-methoxymethyl-4'-(2-methoxyethyl)phenoxy]-propanol-2.

EXAMPLE 5

1-isopropylamino-3-[2'-chloro-4'-(3-methoxy-n-propyl)phenoxy]-propanol-2. Melting point 120° C. Equ. weight: found 353, calculated 352.

EXAMPLE 6

1-isopropylamino-3-[2'-bromo-4'-(3-methoxypropyl)-phenoxy]-propanol-2. Melting point 130° C. Equ. weight: found 400, calculated 397.

EXAMPLE 7

1-isopropyalmino-3-[2'-methoxymethylphenoxy]-propanol-2. Melting point 112° C. Equ. weight: found 313, calculated 320.

EXAMPLE 8

1-isopropylamino-3-[2'-allyl-4'-(2-methoxyethyl)-phenoxyl]propanol-2. Melting point 86° C. Equ. weight: found 346, calculated 344.

EXAMPLE 9

1-isopropylamino-3-[2'-propyl-4'-(2-methoxyethyl)-phenoxy]-propanol-2. Melting point 90° C. Equ. weight: found 347, calculated 346.

In accordance with the method of Example 1 without any addition of HCl, the following compounds were obtained as bases.

EXAMPLE 10

1-isopropylamino-3-[2'-allyl-4'-(3-methoxy-n-propyl)phenoxy]-propanol-2. Melting point: oil. Equ. weight: found 331, calculated 321.

EXAMPLE 11

1-isopropylamino-3-[2'-fluoro-4'-(2-methylmercaptoethyl)phenoxy]-propanol-2xHCl. Melting point 99° C. Equ. weight: found 338, calculated 338.

EXAMPLE 12

1-isopropylamino-3-[2'-methoxy-4'-(3-methoxy-n-propyl)phenoxy]-propanol-2xHCl. Melting point 90° C. Equ. weight: found 327, calculated 322.

EXAMPLE 13

1-isopropylamino-3-[2'-fluoro-4'-(2-methoxyethyl)-phenoxy]-propanol-2xHCl. Melting point 80° C. Equ. weight: found 346, calculated 348.

EXAMPLE 14 (Method B)

A solution of 2-chloro-4-(β-methoxyethyl)-phenylglycidyl ether (10g) in 100 ml of ethanol was saturated with gaseous ammonia and the mixture was then heated in an autoclave on a boiling waterbath during 4 hours. After the solvent was evaporated the residue was dissolved in ethyl acetate and HCl gas was introduced therein. The hydrochloride which precipitated was filtered off and dissolved in 60 ml of ethanol. To the solution 20 ml of isopropyliodide and 15 g of potassium carbonate were added. The mixture was heated in an autoclare at 120° C. during 10 hours where the ethanol had evaporated and the residue was dissolved in 10 ml of 2N HCl and 100 ml of ether. The aqueous phase was separated, made alkaline with 2N NaOH, and extracted with ethyl acetate. The ethyl acetate phase was dried over potassium bicarbonate, and the hydrochloride was precipitated from it with gaseous HCl. The hydrochloride of 1-isopropylamino-3-[2'-chloro-4'-(2-methoxyethyl)-phenoxy]-propanol-2 was obtained. Mp 141° C. Equ. weight: found 338, calculated 338.

EXAMPLE 15 (Method C)

1.2 g of sodium was dissolved in 50 ml of ethanol and to the solution 12.4 g of 2-bromo-4-(2-methoxyethoxy)-phenol and 7.6 g of 1-isopropylamino-3-chloropropanol-2 were added, whereupon the mixture was heated in an autoclave on a boiling waterbath over night. Thereupon it was filtered and the filtrate was evaporated to dryness. To the residue, 2 N HCl was added and the resulting mixture was extracted with ether. The aqueous phase was made alkaline using 2 N NaOH and extracted with ether. The ether phase was dried over potassium carbonate, whereupon the hydrochloride was precipitated with gaseous HCl. The hydrochloride of 1-isopropylamino-3-[2'-bromo-4'-(2-methoxyethyoxy)-phenoxy]-propanol-2 was obtained. Recrystallized from ethylacetate the m.p. was 127° C. Equ. weight: found 401, calculated 399.

EXAMPLE 16 (Method D)

The aforegoing experiment was repeated but instead of 1-isopropylamino-3-chloropropanol-2 an equivalent amount of N-benzyl-1-isopropylamino-3-chloropropanol-2 was used. Thereby the hydrochloride of N-benzyl-1-isopropylamino-3-[2'-bromo-4'-(2-methoxyethoxy)-phenoxy]-propanol-2 was obtained, which was dissolved in ethanol, to which a Pd/C catalyst had been added, and was hydrogenated until the calculated amount of hydrogen had been absorbed. After filtration the filtrate was evaporated to dryness and the residue was recrystallized from ethyl acetate. The melting point obtained was 128° C. Equ. weight: found 398, calculated 399.

EXAMPLE 17 (Method E)

In accordance with the description of method B above, 1-amino-3-[2'-chloro-4'-(2-methoxyethyl)-phenoxy]-propanol-2 was prepared. 5 g. of this compound were dissolved in 50 ml of methanol and 10 ml of acetone. The solution was chilled to 0° C. and at this temperature 5 g. of sodiumborohydride were added little by little. The temperature was then allowed to rise to room temperature, after 1 hour 150 ml of $H_2O$ was added and the solution was extracted with ether. The ether phase was dried over potassium carbonate and evaporated. The residue was transformed into its hydrochloride. 1-isopropylamino-3-[2'-chloro-4'(2-methoxyethyl)-phenoxy]-propanol-2 was obtained having the m.p. 140° C. Equ. weight: found 340, calculated 338.

EXAMPLE 18 (Method H)

18.7 g of 2-chloro-4-(2-methoxyethyl)-phenol were dissolved in a solution of 4.6 g. of sodium in 100 ml of ethanol. To the solution 12.5 g. of 2-hydroxy-3-chloro-propionic acid was added and the resulting mixture was refluxed during 3 hours. Thereupon the solvent was evaporated and to the residue 100 ml of 2 N HCl were added. This was extracted with benzene. The benzene phase was shaken with a sodium bicarbonate solution, which then was made acid using HCl. The aqueous phase was then extracted with benzene and after evaporation 2-hydroxy-3-[2'-chloro-4'-(2-methoxyethyl)-phenoxy]-propionic acid was obtained. The N-isopropylamide was prepared therefrom by dissolving the acid in tetrahydrofuran, adding isopropylamine, and dicyclohexyldicarbodi-imide, and heating at 40° C. for 5 hours. After filtration 5 g of lithium aluminum hydride were added to the filtrate. The filtrate was refluxed over night while stirring. After a preparation in accordance with known methods and transformation to the hydrochloride, the hydrochloride of 1-isopropylamino-3-[2'-chloro-4'-(2-methoxyethyl)-phenoxy]-propanol-2 having a m.p. of 140° C. was obtained. Equ. weight: found 337, calculated 338.

EXAMPLE 19

A syrup containing 2% (weight per volume) of active substance was prepared from the following ingredients:

| | |
|---|---|
| 1-Isopropylamino-3-[2'-bromo-4'-(methoxyethyl)-phenoxy]-propanol-2 . HCl | 2.0 g |
| Saccharine | 0.6 g |
| Sugar | 30.0 g |
| Glycerine | 5.0 g |
| Flavoring agent | 0.1 g |
| Ethanol 96% | 10.0 ml |
| Distilled water | ad 100.0 ml |

Sugar, saccharine and the ethersalt were dissolved in 60 g of warm water. After cooling glycerine and a solution of flavoring agents dissolved in ethanol were added. To the mixture, water was then added to 100 ml.

The above given active substance may be replaced with other pharmaceutically acceptable acid addition salts.

EXAMPLE 20

1-Isopropylamino-3-[2'-chloro-4'-(β-methoxyethyl)-phenoxy]-propanol-2-hydrochloride (250 g) was mixed with lactose (175.8 g), potato starch (169.7 g) and colloidal silicic acid (32 g). The mixture was moistened with a 10% solution of gelatine and was granulated through a 12-mesh sieve. After drying, potato starch (160 g), talc (50 g) and magnesium stearate (5 g) were admixed and the mixture thus obtained was pressed into tablets (10.000) which contain 25 mg of substance. The tablets are sold on the market provided with a breaking score to give another dose than 25 mg or to give multiples thereof when broken.

EXAMPLE 21

Granules can be prepared from 1-isopropylamino-3-[2'-allyl-4'-(β-methoxyethyl)-phenoxy]-propanol-2-hydrochloride (250 g), lactose (175.9 g) and an alcoholic solution of polyvinylpyrrolidone (25 g). After the drying step, the granules can be mixed with talc (25 g), potato starch (40 g) and magnesium stearate (2.50 g) and pressed into 10.000 tablets. These tablets can be prime-coated with a 10% alcoholic solution of shellac and further coated with an aqueous solution containing saccharose (45%), gun arabicum (5%), gelatine (4%) and dyestuff (0.2%). Talc and powder sugar can be used for powdering after the first five coatings. The coating can be then coated with a 66% sugar syrup and polished with a 10% carnauba wax solution in carbon tetrachloride.

EXAMPLE 22

1-isopropylamino-3-[2'-bromo-4'-(β-methoxyethyl)-phenoxy]-propanol-2-hydrochloride (1 g), sodium chloride (0.8 g) and ascorbic acid (0.1 g) can be dissolved in a sufficient amount of distilled water to give 100 ml of solution. This solution, which would contain 10 mg of active substance in each ml, can be used in filling ampoules which would be sterilized by heating at 120° C. for 20 minutes.

PHARMACOLOGICAL EVALUATION

Compounds prepared according to the examples were evaluated for intrinsic activity and blocking effect on heart rate and peripheral vasodilator response to isoprenaline in the cat. Alprenolol was used as a reference source.

Cats weighing between 1.8 and 2.8 kg were anesthetized with 39 mg/kg pentobarbital sodium, intraperitoneally. The cat had been pre-treated with reserpine, 5 mg/kg intramuscular, about 18 hours before the experiment. Bilateral vagotomy was performed before the start of the experiment.

The heart rate was recorded on an Offner cardiotachometer triggered by the EKG-complex. Mean arterial blood pressure was recorded from a carotid artery. The peripheral resistance was measured in one of the legs of the cat in the following way: The femoral artery was opened in the inguinal region and the leg was perfused by blood delivered through a sigma motor pump at constant rate. The flow resistance (the pressure) was recorded via pressure transducer connected to the catheter distally to the pump. The paw was excluded from the circulation by a tight ligature. Intravenously injected isoprenaline increased the heart rate and reduced the perfusion pressure. An isoprenaline dose giving 70–80% of the maximal chronotropic response was determined. This dose (usually 0.1 μg/kg) was then repeated with 20-minute intervals. Ten minutes before each isoprenaline injection, the tested substances were administered intravenously for two minutes, starting with a dose of 0.01 mg/kg and increasing each subsequent dose fourfold. The intrinsic effects of the test substances were determined. The dose producing 50% blockade of the isoprenaline responses was evaluated from the plotted log dose percent blockade diagrams.

Table I shows the results of the foregoing experiments for intrinsic stimulating activity on heart rate in cats, β-blocking activity on heart and peripheral vascular resistance in cats and $LD_{50}$ after intraperitoneal administration in mice of compounds of the formula I

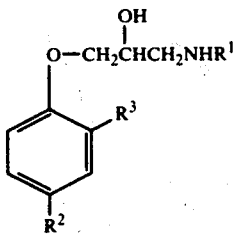

Reference is made to the aforegoing examples only in order to simplify the Table I.

O-allyl (alprenolol) means 1-isopropylamino-3-(2-allyl-phenoxy)-propanol-2.

TABLE I

| Compounds Tested (Figures relate to the above examples and compounds prepared therein) | Reserpinized Cat | | |
|---|---|---|---|
| | Intrinsic activity % of maximal isoprenaline heart rate | β-blockade heart rate $ED_{50}$ mg/kg | β-blockade peripheral vascular resistance $ED_{50}$ mg/kg |
| o-allyl(alprenolol) | 20 | 0.1 | 0.05 |
| 1 | 0 | 0.03 | 1 |
| 2 | 0 | 0.1 | 3 |
| 3 | 0 | 0.03 | 1 |
| 4 | 5 | 0.2 | 5 |
| 5 | 0 | 0.3 | 2 |
| 6 | 0 | 0.4 | 1.5 |
| 7 | 1 | 0.6 | 3 |
| 8 | 0 | 0.1 | 0.8 |
| 9 | 0 | 0.1 | 0.5 |
| 10 | 0 | 0.3 | 1 |
| 11 | 0 | 0.2 | 1 |
| 12 | 0 | 0.4 | 5 |
| 13 | 0 | 0.05 | 2.7 |

The results reported in Table I show that the activity of the phenoxy-hydroxypropylamine test substances according to the invention as regards blockade of β-receptors of the heart varied from about 1/6 to 3.3 times the activity of alprenolol. The peripheral vascular β-blocking activity for the test substances was 10–100 times lower than the activity of alprenolol. The results demonstrate that the test substances, developed a relatively stronger blockade of the β-receptors of the heart than of the receptors in smooth muscles. Due to this cardioselectivity, the compounds according to the invention give therapeutic effects in treating cardiovascular diseases without risk or complications due to β-blockade in bronchi and blood vessels.

Results similar to the foregoing on reserpinized cats can be expected when the compounds are tested to determine the decrease in exercise tachycardia in running dogs (running on an endless belt at a rate of 7 km per hour).

We claim:

1. A compound of the formula

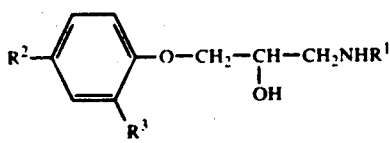

or a pharmaceutically acceptable non-toxic acid addition salt thereof, wherein $R^1$ is an alkyl or hydroxyalkyl radical of 1 to 4 carbon atoms; $R^2$ is selected from the group consisting of alkoxymethyl and alkoxyethyl in which the alkoxy part contains 1 to 4 carbon atoms; and $R^3$ is selected from the group consisting of halogen, alkenyl of 2 to 4 carbon atoms and alkoxymethyl having 2 to 4 carbon atoms.

2. A compound according to 1, wherein $R^1$ is an alkyl group of 1 to 4 carbon atoms; $R^2$ is selected from the group consisting of methoxymethyl and methoxyethyl; and $R^3$ is selected from the group consisting of halogen and methoxymethyl.

3. A compound according to claim 1 in racemic form.

4. A compound according to claim 1 resolved into its optically active, levo-rotary isomer.

5. A compound according to claim 1 resolved into its optically active, dextro-rotary isomer.

6. The compound according to claim 1 which is 1-[2-bromo-4-(2-methoxyethyl)-phenoxy]-3-isopropylaminopropanol-2 or a pharmaceutically acceptable salt thereof.

7. The compound according to claim 1 which is 1-[2-chloro-4-(2-methoxyethyl)-phenoxy]-3-isopropylaminopropanol-2 or a pharmaceutically acceptable salt thereof.

8. The compound according to claim 1 which is 1-[2-chloro-4-(2-methoxyethyl)-phenoxy]-3-tert.-butylaminopropanol-2 or a pharmaceutically acceptable salt thereof.

9. The compound according to claim 1 which is 1-[2-methoxymethyl-4-(2-methoxyethyl)-phenoxy]-3-isopropylaminopropanol-2 or a pharmaceutically acceptable salt thereof.

10. The compound according to claim 1 which is 1-[2-allyl-4-(2-methoxyethyl)-phenoxy]-3-isopropylaminopropanol-2 or a pharmaceutically acceptable salt thereof.

11. The compound according to claim 1 which is 1-[2-fluoro-4-(2-methoxyethyl)-phenoxy]-3-isopropylamino-propanol-2or a pharmaceutically acceptable salt thereof.

12. A compound of the formula

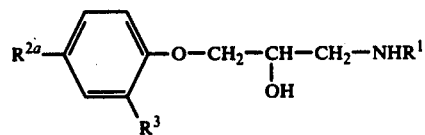

or a pharmaceutically acceptable non-toxic acid addition salt thereof, wherein $R^1$ is an alkyl or hydroxyalkyl radical of 1 to 4 carbon atoms; $R^{2a}$ is an alkoxyethyl group in which the alkoxy part contains 1 to 4 carbon atoms; and $R^3$ is selected from the group consisting of halogen, alkenyl of 2 to 4 carbon atoms and alkoxymethyl of 2 to 4 carbon atoms.

13. A compound of the formula

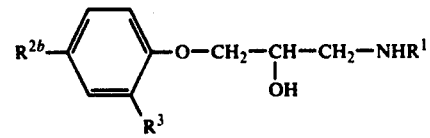

or a pharmaceutically acceptable non-toxic acid addition salt thereof, wherein $R^1$ is an alkyl or hydroxyalkyl radical of 1 to 4 carbon atoms; $R^{2b}$ is a methoxyethyl group; and $R^3$ is selected from the group consisting of halogen, alkenyl of 2 to 4 carbon atoms and alkoxymethyl of 2 to 4 carbon atoms.

14. A pharmaceutical preparation providing cardioselective antagonism to adrenergic β-receptor stimulation containing as an active ingredient a dosage unit effective to provide said cardioselective antagonism to adrenergic β-receptor stimulation, an ortho-para-substituted phenoxy-hydroxypropylamine compound of the formula

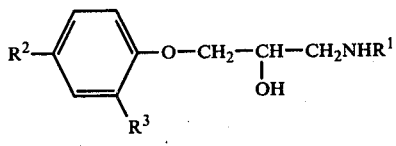

or a pharmaceutically acceptable non-toxic acid addition salt thereof, wherein $R^1$ is an alkyl or hydroxyalkyl radical of 1 to 4 carbon atoms; $R^2$ is selected from the group consisting of alkoxymethyl and alkoxyethyl in which the alkoxy part contains 1 to 4 carbon atoms; and $R^3$ is selected from the group consisting of halogen, alkenyl of 2 to 4 carbon atoms and alkoxymethyl having 2 to 4 carbon atoms, together wth a pharmaceutically acceptable carrier.

15. A pharmaceutical preparation according to claim 14, wherein $R^1$ is an alkyl group of 1 to 4 carbon atoms; $R^2$ is selected from the group consisting of methoxymethyl and methoxyethyl; and $R^3$ is selected from the group consisting of halogen and methoxymethyl.

16. A pharmaceutical preparation according to claim 14 wherein the active ingredient is a therapeutically effective dose of at least one said compound in racemic form.

17. A pharmaceutical preparation according to claim 14 wherein the active ingredient is a therapeutically effective dose of at least one of said compounds as the optically active, dextro-rotary isomer.

18. A pharmaceutical preparation according to claim 14 wherein the active ingredient is a therapeutically effective dose of at least one of said compounds as the optically active, levo-rotary isomer.

19. A pharmaceutical preparation according to claim 14 wherein the ortho-para-substituted phenoxy-hydroxypropylamine compound comprises 0.1 to 95% by weight of the preparation.

20. A pharamaceutical preparation according to claim 14 in a form suitable for administration by injection wherein the ortho-para-substituted phenoxy-hydroxyproylamine compound comprises about 0.5% to about 20% by weight of the preparation.

21. A pharmaceutical preparation according to claim 14 for parenteral application which comprises an aqueous solution of a water soluble salt of said ortho-para-substituted phenoxy-hydroxypropylamine compound in an amount of about 0.5–10% by weight of the preparation.

22. A pharmaceutical preparation according to claim 14 in a form suitable for oral administration wherein the ortho-para-substituted phenoxy-hydroxypropylamine compound comprises about 0.2% to about 50% by weight of the preparation.

23. A pharmaceutical preparation according to claim 14 wherein the active ingredient is 1-[2-bromo-4-(2-methoxyethyl)-phenoxy]-3-isopropylaminopropanol-2 or a pharmaceutically acceptable non-toxic addition salt thereof.

24. A pharmaceutical preparation according to claim 14 wherein the active ingredient is 1-[2-chloro-4-(2-methoxyethyl)-phenoxy]-3-isopropylaminopropanol-2 or a pharmaceutically acceptable non-toxic addition salt thereof.

25. A pharmaceutical preparation according to claim 14 wherein the active ingredient is 1-[2-chloro-4-(2-methoxyethyl)-phenoxy]-3-tert.-butylaminopropanol-2 or a pharmaceutically acceptable non-toxic addition salt thereof.

26. A pharmaceutical preparation according to claim 14 wherein the active ingredient is 1-[2-methoxymethyl-4-(2-methoxyethyl)-phenoxy]-3-ispropylaminopropanol-2 or a pharmaceutically acceptable non-toxic addition salt thereof.

27. A pharmaceutical preparation according to claim 14 wherein the active ingredient is 1-[2-allyl-4-(2-methoxyethyl)-phenoxy]-3-isopropylaminopropanol-2 or a pharmaceutically acceptable non-toxic addition salt thereof.

28. A pharmaceutical preparation according to claim 14 wherein the active ingredient is 1-[2-fluoro-4-(2-methoxyethyl)-phenoxy]-3-isopropylaminopropanol-2 or a pharmaceutically acceptable non-toxic addition salt thereof.

29. A pharmaceutical preparation providing cardioselective antagonism to adrenergic β-receptor stimulation containing as an active ingredient a dosage unit effective to provide said cardioselective antagonism to adrenergic β-receptor stimulation, an ortho-para-substituted phenoxy-hydroxypropylamine compound of the formula

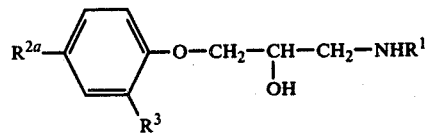

or a pharmaceutically acceptable non-toxic acid addition salt thereof, wherein $R^1$ is an alkyl or hydroxyalkyl radical of 1 to 4 carbon atoms; $R^{2a}$ is an alkoxyethyl group in which the alkoxy part contains 1 to 4 carbon atoms; and $R^3$ is selected from the group consisting of halogen, alkenyl of 2 to 4 carbon atoms and alkoxymethyl of 2 to 4 carbon atoms, together with a pharmaceutically acceptable carrier.

30. A pharmaceutical preparation providing cardioselective antagonism to adrenergic β-receptor stimulation containing as an active ingredient a dosage unit effective to provide said cardioselective antagonism to adrenergic β-receptor stimulation, an ortho-para-substituted phenoxy-hydroxypropylamine compound of the formula

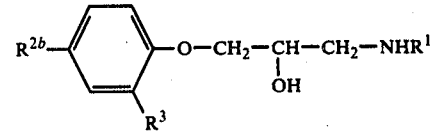

or a pharmaceutically acceptable non-toxic acid addition salt thereof, wherein $R^1$ is an alkyl or hydroxyalkyl radical of 1 to 4 carbon atoms; $R^{2b}$ is methoxyethyl; and $R^3$ is selected from the group consisting of halogen, alkenyl of 2 to 4 carbon atoms and alkoxymethyl having 2 to 4 carbon atoms, together with a pharmaceutically acceptable carrier.

31. A method providing for cardioselective antagonism to adrenergic β-receptor stimulation in an animal which comprises administering an amount effective to provide said cardioselective antagonism to adrenergic β-receptor stimulation of an ortho-para-substituted phenoxy-hydroxypropylamine compound of the formula

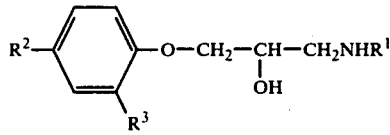

or a pharmaceutically acceptable non-toxic acid addition salt thereof, wherein $R^1$ is an alkyl or hydroxyalkyl radical of 1 to 4 carbon atoms; $R^2$ is selected from the group consisting of alkoxymethyl and alkoxyethyl in which the alkoxy part contains 1 to 4 carbon atoms; and $R^3$ is selected from the group consisting of halogen, alkenyl of 2 to 4 carbon atoms and alkoxymethyl having 2 to 4 carbon atoms.

32. A method according to claim 31, wherein $R^1$ is an alkyl group of 1 to 4 carbon atoms; $R^2$ is selected from the group consisting of methoxymethyl and methoxyethyl; and $R^3$ is selected from the group consisting of halogen and methoxymethyl.

33. A method according to claim 31 wherein the phenoxyhydroxypropylamine compound is 1-[2-bromo-4-(2-methoxyethyl)-phenoxy]-3-isopropylamino-propanol-2 or a pharmaceutically acceptable salt thereof.

34. A method according to claim 31 wherein the phenoxyhydroxypropylamine compound is 1-[2-chloro-4-(2-methoxyethyl)-phenoxy]-3-isopropylamino-propanol-2 or a pharmaceutically acceptable salt thereof.

35. A method according to claim 31 wherein the phenoxyhydroxypropylamine compound is 1-[2-chloro-4-(2-methoxyethyl)-phenoxy]-3-tert.-butylamino-propanol-2 or a pharmaceutically acceptable salt thereof.

36. A method according to claim 31 wherein the phenoxyhydroxypropylamine compound is 1-[2-methoxymethyl-4-(2-methoxyethyl)-phenoxy]-3-isopropylaminopropanol-2 or a pharmaceutically acceptable salt thereof.

37. A method according to claim 31 wherein the phenoxyhydroxypropylamine compound is 1-[2-allyl-4-(2-methoxyethyl)-phenoxy]-3-isopropylaminopropanol-2 or a pharmaceutically acceptable salt thereof.

38. A method according to claim 31 wherein the phenoxyhydroxypropylamine compound is 1-[2-fluoro-4-(2-methoxyethyl)-phenoxy]-3-isopropylamino-propanol-2 or a pharmaceutically acceptable salt thereof.

39. A method providing for cardioselective antagonism to adrenergic β-receptor stimulation in an animal which comprises administering an amount effective to provide said cardioselective antagonism to adrenergic β-receptor stimulation of an ortho-para-substituted phenoxy-hydroxy propylamine compound of the formula

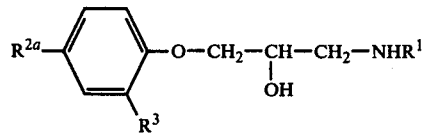

or a pharmaceutically acceptable non-toxic acid addition salt thereof, wherein $R^1$ is an alkyl or hydroxyalkyl radical of 1 to 4 carbon atoms; $R^{2a}$ is an alkoxyethyl group in which the alkoxy part contains 1 to 4 carbon atoms; and $R^3$ is selected from the group consisting of halogen, alkenyl of 2 to 4 carbon atoms and alkoxymethyl having 2 to 4 carbon atoms.

40. A method providing for cardioselective antagonism to adrenergic β-receptor stimulation in an animal which comprises administering an amount effective to provide said cardioselective antagonism to adrenergic β-receptor stimulation of an ortho-para-substituted phenoxy-hydroxy propylamine compound of the formula

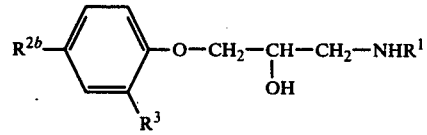

or a pharmaceutically acceptable non-toxic acid addition salt thereof, wherein $R^1$ is an alkyl or hydroxyalkyl radical of 1 to 4 carbon atoms; $R^{2b}$ is methoxyethyl; and $R^3$ is selected from the group consisting of halogen, alkenyl of 2 to 4 carbon atoms and alkoxymethyl having 2 to 4 carbon atoms.

* * * * *

UNITED STATES PATENT OFFICE
CERTIFICATE OF CORRECTION

Patent No. 4,145,442          Dated March 20, 1979

Inventor(s) Peder B. Berntsson et al.

It is certified that error appears in the above-identified patent and that said Letters Patent are hereby corrected as shown below:

Col. 1, line 39, "alkly" should be --alkyl--;
Col. 4, line 7, "lboratory" should be --laboratory--;
Col. 4, line 27, "opoxy" should be --epoxy--;
Col. 6, line 20, "s" should be --as--;
Col. 9, line 54, "nown" should be --known--;
Col. 10, line 52, "chromatorgraphy" should be --chromatography--;
Col. 13, line 8, "1-tert.-butylamino-3-[2'-(2-methoxyethyl)-phenoxy]" should be --1-tert.-butylamino-3-[2'-chloro-4'-(2-methoxyethyl)-phenoxy]--;
Col. 18, line 36, "-2or" should be -- -2 or --;
Col. 19, line 45, "pharamaceutical" should be --pharmaceutical--;
Col. 19, line 48, "hydroxyproylamine" should be --hydroxypropylamine--.

Signed and Sealed this

Twenty-sixth Day of February 1980

[SEAL]

Attest:

Attesting Officer

SIDNEY A. DIAMOND

Commissioner of Patents and Trademarks